(12) United States Patent
Banju et al.

(10) Patent No.: US 7,854,749 B2
(45) Date of Patent: Dec. 21, 2010

(54) SURGICAL GRIPPER

(75) Inventors: Kazuo Banju, Hachioji (JP); Shuhei Iizuka, Hamamatsu (JP); Manabu Miyamoto, Hachioji (JP); Nobuaki Akui, Hino (JP)

(73) Assignee: Olympus Corporation (JP)

( * ) Notice: Subject to any disclaimer, the term of this patent is extended or adjusted under 35 U.S.C. 154(b) by 0 days.

(21) Appl. No.: 11/414,708

(22) Filed: Apr. 28, 2006

(65) Prior Publication Data

US 2006/0195140 A1    Aug. 31, 2006

Related U.S. Application Data

(63) Continuation of application No. PCT/JP2005/004650, filed on Mar. 16, 2005.

(30) Foreign Application Priority Data

Mar. 26, 2004    (JP)    ............................... 2004-093121

(51) Int. Cl.
    *A61B 17/00* (2006.01)
(52) U.S. Cl. ...................................... 606/205; 606/139
(58) Field of Classification Search ................ 606/139, 606/1, 205; 112/169, 221, 222, 225, 226; 223/99; 269/6, 3, 95, 254 CS
    See application file for complete search history.

(56) References Cited

U.S. PATENT DOCUMENTS

| | | | | |
|---|---|---|---|---|
| 4,763,669 A | * | 8/1988 | Jaeger | 600/564 |
| 5,242,458 A | | 9/1993 | Bendel et al. | 606/147 |
| 5,250,056 A | | 10/1993 | Hasson | 606/151 |
| 5,437,682 A | * | 8/1995 | Grice et al. | 606/148 |
| 5,449,366 A | * | 9/1995 | Li | 606/147 |
| 5,746,753 A | * | 5/1998 | Sullivan et al. | 606/147 |
| 6,280,458 B1 | | 8/2001 | Boche et al. | 606/206 |
| 7,291,161 B2 | * | 11/2007 | Hooven | 606/205 |
| 2002/0040217 A1 | * | 4/2002 | Jinno | 606/1 |

(Continued)

FOREIGN PATENT DOCUMENTS

EP    0 674 878 A1    10/1995

(Continued)

OTHER PUBLICATIONS

International Search Report PCT/JP2005/004650 dated Jun. 10, 2005.

(Continued)

*Primary Examiner*—Todd E Manahan
*Assistant Examiner*—Katherine M Dowe
(74) *Attorney, Agent, or Firm*—Ostrolenk Faber LLP

(57) ABSTRACT

A surgical gripper includes a gripping section opened/closed to grip an object to be gripped and an operation section which opens/closes the gripping section, wherein the gripping section is configured to be opened/closed by the operation section to take a gripping mode of gripping the object to be gripped so that treatment is performed by the object to be gripped, an adjusting mode of gripping the object to be gripped by a gripping force lower than that of the gripping mode so that an arrangement of the object to be gripped is adjusted while the object to be gripped is held, and a releasing mode of releasing the object to be gripped.

1 Claim, 3 Drawing Sheets

U.S. PATENT DOCUMENTS

2005/0159764 A1 * 7/2005 Kasahara et al. ............ 606/159

FOREIGN PATENT DOCUMENTS

| EP | 0 732 078 A2 | 9/1996 |
| EP | 0 732 078 A3 | 9/1996 |
| JP | 6-296618 | 10/1994 |
| JP | 7-265326 | 10/1995 |
| JP | 2002-59380 | 2/2002 |
| WO | WO 93/21833 | 11/1993 |

OTHER PUBLICATIONS

English translation of Notification of Transmittal of Preliminary Report on Patentability dated Oct. 5, 2006 for PCT/JP2005/004650.
European Search Report dated Dec. 16, 2008 in connection with the corresponding European Application No. 05720904.1.

* cited by examiner

SURGICAL GRIPPER

CROSS-REFERENCE TO RELATED APPLICATIONS

This is a Continuation Application of PCT Application No. PCT/JP2005/004650, filed Mar. 16, 2005, which was published under PCT Article 21(2) in Japanese.

This application is based upon and claims the benefit of priority from prior Japanese Patent Application No. 2004-093121, filed Mar. 26, 2004, the entire contents of which are incorporated herein by reference.

BACKGROUND OF THE INVENTION

1. Field of the Invention

The present invention relates to a surgical gripper which grips an instrument such as an anastomotic needle and operates the instrument in the gripped state to perform treatment.

2. Description of the Related Art

When an anastomotic operation is carried out in a body cavity under endoscopic observation, a needle holder that grips an anastomotic needle is used. An example of such a needle holder is disclosed in Jpn. Pat. Appln. KOKAI Publication No. 7-265326. According to this needle holder, application of an excessive gripping force on an anastomotic needle to be gripped is prevented. In other words, according to the needle holder, a gripping section that grips the anastomotic needle is opened/closed by an operation handle. Then, a gripping force of the anastomotic needle by the gripping section is decided based on an operation force of the operation handle. An elastic member is disposed in the operation handle to absorb an operation force so that application of an excessive gripping force on the anastomotic needle can be prevented even when a large operation force more than necessary is applied on the operation handle.

BRIEF SUMMARY OF THE INVENTION

An embodiment of the present invention is directed to a surgical gripper which includes a gripping section opened/closed to grip an object to be gripped and an operation section which opens/closes the gripping section, wherein the gripping section is configured to be opened/closed by the operation section to take a gripping mode of gripping the object to be gripped so that treatment is performed by the object to be gripped, an adjusting mode of gripping the object to be gripped by a gripping force lower than that of the gripping mode so that an arrangement of the object to be gripped is adjusted while the object to be gripped is held, and a releasing mode of releasing the object to be gripped.

BRIEF DESCRIPTION OF THE SEVERAL VIEWS OF THE DRAWING

The accompanying drawings, which are incorporated in and constitute a part of the specification, illustrate embodiments of the invention, and together with the general description given above and the detailed description of the embodiments given below, serve to explain the principles of the invention.

DETAILED DESCRIPTION OF THE INVENTION

Figure 1A:
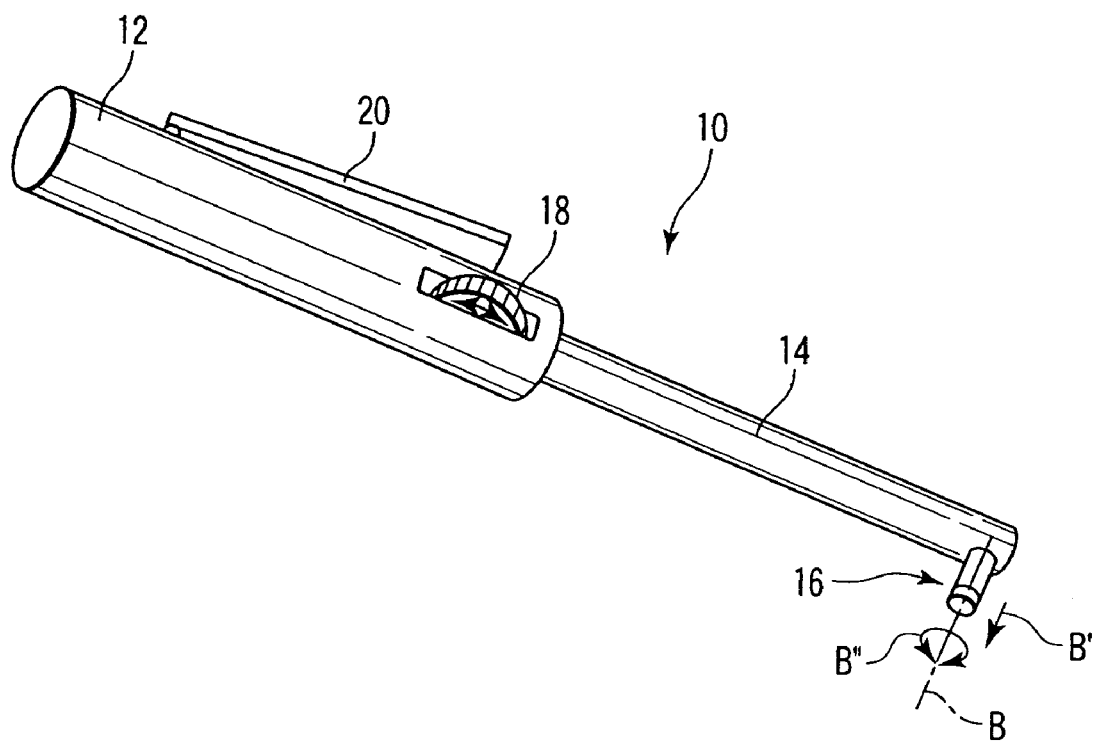
FIG. 1A is a perspective view showing a needle holder according to a first embodiment of the present invention.
Figure 1B:
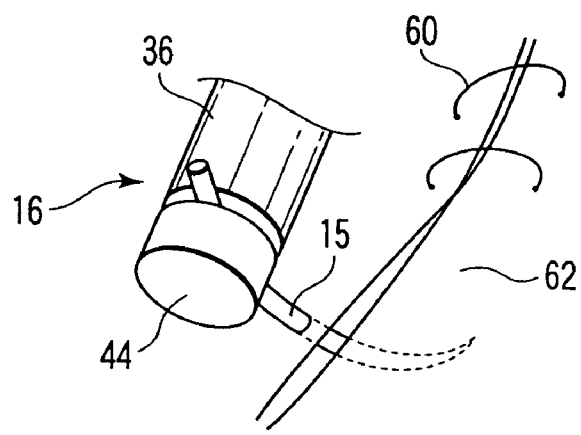
FIG. 1B is an explanatory view of a situation in which an anastomotic needle is gripped by the needle holder of the first embodiment of the present invention to anastomose blood vessels.

Next, a first embodiment of the present invention will be described by referring to FIGS. 1A to 3. According to the embodiment, as shown in FIGS. 1A and 1B, a surgical needle holder 10 as a surgical gripper is used to grip an anastomotic needle 15 and perform anastomotic treatment. This surgical needle holder 10 has a thin and long body section 12 held by an operator. A thin and long insertion section 14, which is inserted into a body cavity of a patient, extends from the body section 12. In an extended end of the insertion section 14, arranged is a needle holding section 16 as a gripping section which is opened/closed to grip the anastomotic needle 15.

The needle holding section 16 projects in a direction of an axis B (direction of an arrow B') vertical to a longitudinal axis of the insertion section 14 and is able to rotate around the axis B (direction of an arrow B"). The needle holding section 16 is connected to a gripping section rotation dial 18 arranged in the body section 12 by transmission means formed by a belt, a pulley or the like. By rotating the gripping section rotation dial 18, the needle holding section 16 is rotated around the axis B (direction of the arrow B"). Additionally, the needle holding section 16 is connected to an opening/closing lever 20 arranged in the body section 12. By opening/closing the opening/closing lever 20, the needle holding section 16 is opened/closed. The gripping section rotation dial 18 and the opening/closing lever 20 are arranged in the body section 12 to be operated while the operator holds the body section 12.

Figure 2:
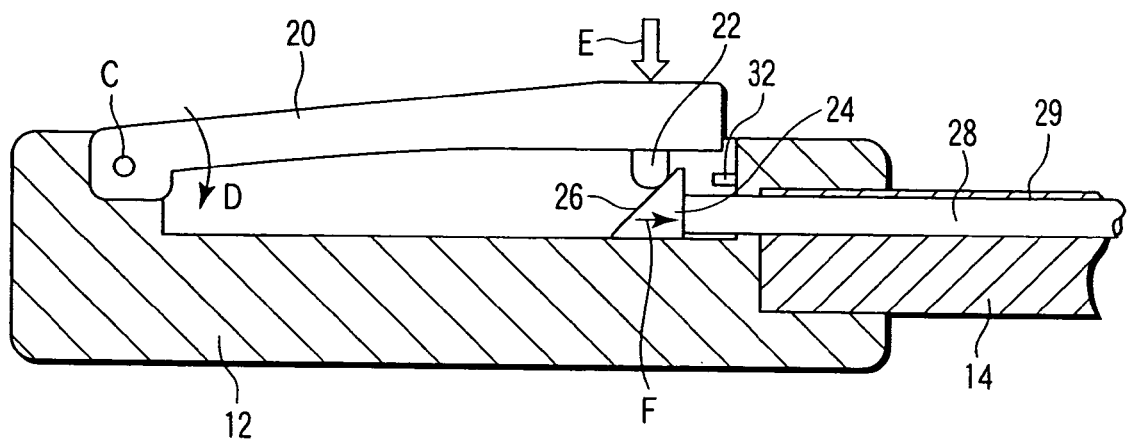
FIG. 2 is a longitudinal sectional view of an opening/closing lever and its surroundings in the needle holder of the first embodiment of the present invention.

As shown in FIG. 2, one end of the opening/closing lever 20 is pivotally supported on the body section 12, and the opening/closing lever 20 is able to rotate around a rotary shaft C with respect to the body section 12 (see arrow D). In other words, a rotational end of the opening/closing lever 20 is pushed in or is applied to an operation force in a direction toward the body section 12 (direction of an arrow E), whereby the rotational end of the opening/closing lever 20 rotates in the direction toward the body section 12 (direction of the arrow E).

In the rotational end of the opening/closing lever 20, a push pin 22 integrally projects to face the body section 12. A projected end of the push pin 22 is semispherical, and in contact with a first slope 26 of a slope block 24. This slope block 24 can slide in a longitudinal direction of the body section 12, and its first slope 26 faces a rear end side. When the push pin 22 is rotated toward the body section 12 by rotation of the opening/closing lever 20, the slope block 24 is pressed by the push pin 22 to slide to a distal end side (direction of an arrow F) with respect to the body section 12.

The slope block 24 is integrally connected to one end of a slide rod 28. This slide rod 28 is inserted into an insertion hole 29 formed in a longitudinal axis direction of the body section 12 and the insertion section 14 to be able to slide in the longitudinal axis direction of the body section 12 and the insertion section 14. When the slope block 24 is slid to the distal end side by the push pin 22, the slide rod 28 is slid to the distal end side integrally with the slope block 24.

Incidentally, a stopper 32 is arranged in the body section 12 to regulate a rotational range of the opening/closing lever 20. That is, this stopper 32 projects in a moving path of the rotational end of the opening/closing lever 20. When the rotational end of the opening/closing lever 20 is pushed in and operated, a distal end of the stopper 32 abuts on the rotational end of the opening/closing lever 20 to regulate the rotational range of the opening/closing lever 20.

Figure 3:
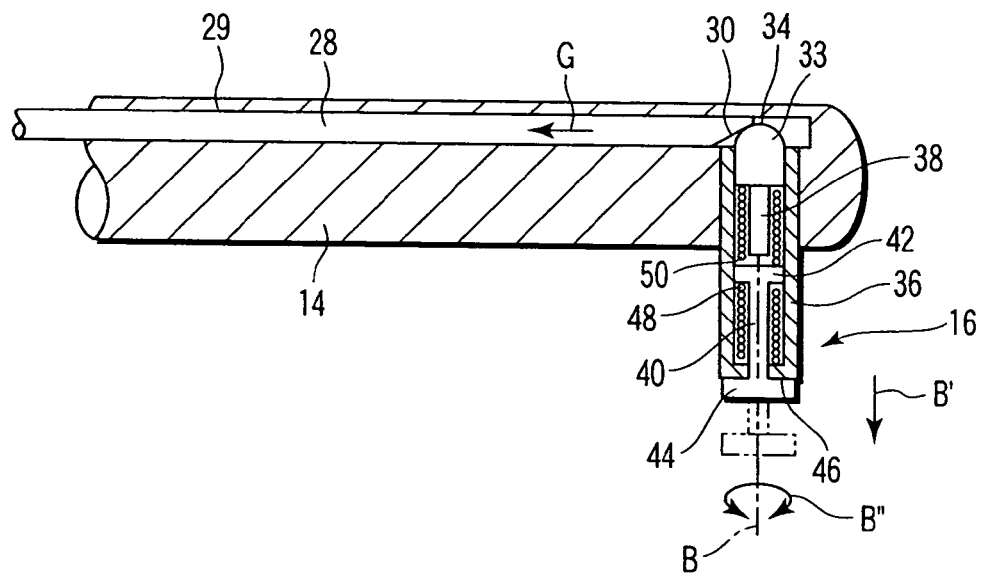
FIG. 3 is a longitudinal sectional view of a distal end part of an insertion section in the needle holder of the first embodiment of the present invention.

As shown in FIG. 3, the insertion hole 29 is connected to a proximal end of the needle holding section 16 of the distal end of the insertion section 14. The other end of the slide rod 28 inserted into the insertion hole 29 is arranged near the proximal end of the needle holding section 16. The other end of the slide rod 28 is formed into a tapered shape and thus a second slope 30 is formed on the needle holding section 16 side in the other end of the slide rod 28.

The second slope 30 always abuts on a semispherical bearing reception surface 34 formed in an inner end of a slide bearing 33 of the needle holding section 16. This slide bearing 33 has a cylindrical shape having the semispherical bearing surface 34 formed in the inner end, and the semispherical shape of the bearing surface 34 and the cylindrical shape are equal to each other in radius. The slide bearing 33 is fitted in an inner end side of a cylindrical tube 36 to be able to slide in a center axis direction of the tube 36.

The tube 36 projects in the direction of the axis B (direction of the arrow B') vertical to the longitudinal axis direction of the insertion section 14 and is able to rotate around the axis B (direction of the arrow B"). The tube 36 is rotated around the axis B (direction of the arrow B") by rotating the gripping section rotation dial 18 (FIG. 1A), whereby the entire needle holding section 16 is rotated around the axis B (direction of the arrow B") as described above.

A pressing section 38 projects in an outer end surface of the slide bearing 33. This pressing section 38 is formed into a rod shape smaller in diameter than the slide bearing 33, and arranged coaxially to the slide bearing 33. When the slide bearing 33 slides outward (direction of the arrow B') with respect to the tube 36, an outer end of the pressing section 38 presses a flange 42 of an inner end of a push rod 40 as a movable member. In other words, the slide bearing 33 and the pressing section 38 form an operation member for operating the push rod 40. The flange 42 is fitted in the tube 36 to be able to slide in a center axis direction of the tube 36. When the flange 42 is pressed outward by the pressing section 38, the entire push rod 40 is moved outward.

An outer end of the push rod 40 is inserted into an opening formed in an outer end wall of the tube 36 to project to the outside. A disk-shaped gripping member 44 is formed in the outer end of the push rod 40 to be roughly parallel to the outer end wall of the tube 36, and a diameter of the gripping member 44 is roughly equal to that of the tube 36. A gripping surface 46 is formed in an outer surface of the outer end wall of the tube 36. When the push rod 40 is moved outward, a gap is generated between the gripping surface 46 and the gripping member 44 to enable arrangement of an anastomotic needle 15 (FIG. 1A) as an object to be gripped between them.

Between an inner surface of the outer end wall of the tube 36 and the outer end surface of the flange 42 of the push rod 40, a first compression spring 48 as a first elastic member is disposed around the push rod 40. The push rod 40 is pressed to the inside by an elastic force of the first compression spring 48. Additionally, between an inner end surface of the flange 42 of the push rod 40 and the outer end surface of the slide bearing 33, a second compression spring 50 as a second elastic member is disposed around the pressing section 38. By an elastic force of the second compression spring 50 the push rod 40 is pressed outward and the slide bearing 33 is pressed inward.

The elastic force of the first compression spring 48 is set larger than that of the second compression spring 50 in all estimated compressing amounts of the first and second compression springs 48 and 50.

Referring to FIGS. 1A to 3, a gripping mode, an adjusting mode, and a releasing mode that the needle holding section 16 can take will be described below.

In the gripping mode, the push rod 40 is pressed inward by the elastic force of the first compression spring 48 to grip and hold the anastomotic needle 15 between the gripping surface 46 of the tube 36 and the gripping member 44. A gripping force of the anastomotic needle 15 is decided based on a difference in elastic force between the first and second compression springs 48 and 50. In the gripping mode, anastomosing by the anastomotic needle 15 needs a sufficient gripping force in order to prevent an unintended movement of the anastomotic needle 15 with respect to the needle holding section 16 caused by resistance when the anastomotic needle 15 is punctured in a organism tissue. The elastic forces of the first and second compression springs 48, 50 are set to realize such a gripping force.

In the adjusting mode, the opening/closing lever 20 of the body section 12 is pushed in more by an amount than in the gripping mode. Then, the slide rod 28 is pushed into the distal end side by an amount and by the second slope 30 of the slide rod 28 the slide bearing 33 is pressed to move outward by an amount. The pressing section 38 of the slide bearing 33 is in contact with the flange 42 of the push rod 40 without being pressed.

By the slide bearing 33 and the push rod 40 the second compression spring 50 is compressed by an amount. On the other hand, as the elastic force of the first compression spring 48 is larger than that of the second compression spring 50, the first compression spring 48 is hardly compressed. Thus, between the gripping mode and the adjusting mode, the opening/closing lever 20 is pushed in mainly against the elastic force of the second compression spring 50, and an operation force necessary for pushing in the opening/closing lever 20 is decided mainly by the elastic force of the second compression spring 50.

The second compression spring 50 is compressed by the slide bearing 33 and the push rod 40, so its elastic force is increased. Accordingly, an outward pressing force from the second compression spring 50 to the push rod 40 is increased to weaken a gripping force of the anastomotic needle 15 by the gripping surface 46 of the tube 36 and the gripping member 44. The adjusting mode needs a gripping force lower than that in the gripping mode or sufficient to easily change a position, a direction or the like of the anastomotic needle 15 with respect to the needle holding section 16 while maintaining the gripped state of the anastomotic needle 15. The elastic forces of the first and second compression springs 48 and 50 are set to realize the gripping force.

In the releasing mode, the opening/closing lever 20 of the body section 12 is pushed in until it abuts on the stopper 32. Then, the slide rod 28 is pushed in to a maximum limit to move the slide bearing 33 outward to a maximum limit. The push rod 40 is pressed by the pressing section 38 of the slide bearing 33 to move outward to a maximum limit, and the gripping member 44 is moved outward to a maximum limit as indicated by a broken line in FIG. 3. In the releasing mode, a gap width between the gripping surface 46 of the tube 36 and the gripping member 44 is set larger than a thickness of the anastomotic needle 15, and the anastomotic needle 15 is released from the needle holding section 16.

Between the adjusting mode and the releasing mode, the pressing section 38 is pressed to the push rod 40. As no change occurs in distance between the slide bearing 33 and the push rod 40, the second compression spring 50 is not compressed anymore while the first compression spring 48 is compressed. Additionally, between the adjusting mode and the releasing mode, the opening/closing lever 20 is pushed in against the elastic forces of the first and second compression springs 48 and 50, and an operation force necessary for pushing in the opening/closing lever 20 is decided mainly based on a sum of the elastic forces of the first and second compression springs 48 and 50.

As described above, the operation force necessary for pushing in the opening/closing lever 20 is decided mainly based on the elastic force of the second compression spring 50 between the gripping mode and the adjusting mode, and mainly based on the sum of the elastic forces of the first and second compression springs 48 and 50 between the adjusting mode and the releasing mode. Hence, in the adjusting mode, the operation force necessary for pushing in the opening/closing lever 20 increases in stages by an amount equivalent to the elastic force of the first compression spring 48. The increase of the operation force of the opening/closing lever 20 is sensed by an operator by means of the sense of touch.

That is, the second compression spring 50 forms a feedback mechanism which changes the operation force of the opening/closing lever 20 necessary for operating the needle holding section 16 when the needle holding section 16 switches from the gripping mode to the adjusting mode, and feeds back the state change of the needle holding section 16. By setting the elastic force of the first compression spring 48 sufficiently larger than that of the second compression spring 50, an increase of the operation force in the adjusting mode becomes conspicuous, so it is easier for the operator to sense the increase.

In a normal mode in which a gripping operation is not carried out by the needle holding section 16, the gripping member 44 abuts on the gripping surface 46 of the tube 36 by the elastic forces of the first and second compression springs 48 and 50, and the slide bearing 33 is pressed inward. The slide rod 28 is pressed to the body section 12 side (direction of an arrow G) by the slide bearing 33. Further, the slope block 24 is pressed together with the slide rod 28, the push pin 22 of the opening/closing lever 20 is pushed up by the first slope 26 of the slope block 24, and the opening/closing lever 20 is held in a standby position in which it is pushed up to a maximum limit.

According to the embodiment, the opening/closing lever 20, the push rod 22, the slope block 24, the slide rod 28, the slide bearing 33, and the pressing section 38 form the operation section for opening/closing the needle holding section 16.

Next, an operation of the needle holder 10 of the embodiment will be described. A case in which the needle holder 10 is used for an operation in an abdominal cavity under endoscopic observation will be described below. First, by a grasping forceps or the like, the anastomotic needle 15 is introduced into the abdominal cavity beforehand through a tracker or the like. Subsequently, an operation of gripping the anastomotic needle 15 by the needle holding section 16 of the needle holder 10 is carried out under endoscopic observation.

In other words, the operator pushes in the opening/closing lever 20 from the standby position until it abuts on the stopper 32, and holds the opening/closing lever 20 in a maximum rotation position. As a result, the gripping member 44 of the needle holding section 16 is separated from the gripping surface 46 of the tube 36 to a maximum limit, whereby the anastomotic needle 15 can be arranged between the gripping member 44 and the gripping surface 46.

Next, the anastomotic needle 15 is arranged between the gripping member 44 and the gripping surface 46 and, after that, pressing applied to the opening/closing lever 20 is release. As a result, the push rod 40 is moved inward by the elastic force of the first compression spring 48 to close the gripping member 44 to the gripping surface 46. Then, the anastomotic needle 15 is held between the gripping member 44 and the gripping surface 46 by the strong elastic force of the first compression spring 48 so that it can be gripped firmly by a strong gripping force. The slide bearing 33, the slide rod 28, and the slope block 24 are pushed back by the elastic forces of the first and second compression springs 48 and 50 to push up the push rod 40 and the opening/closing lever 20.

Thus, the needle holding section 16 is set in the gripping mode, the anastomotic needle 15 firmly gripped by the needle holder 10 is used and, for example, as shown in FIG. 1B, the anastomotic needle 15 is operated to stitch blood vessels together by a thread 60.

When the anastomotic needle 15 is gripped or another anastomosing operation is newly carried out, a position, a direction or the like of the anastomotic needle 15 with respect to the needle holding section 16 may be improper for a desired anastomosing operation. In such a case, the position, the direction or the like of the anastomotic needle 15 with respect to the needle holding section 16 is adjusted.

That is, the opening/closing lever 20 is pushed in, the pushing-in is stopped when the operation force necessary for pushing in the opening/closing lever 20 is increased in stages, and the opening/closing lever 20 is held in this position. During the pushing-in of the opening/closing lever 20, the opening/closing lever 20 is pushed in mainly against the elastic force of the second compression spring 50. When the pressing section 38 comes into contact with the push rod 40, the opening/closing lever 20 is pushed in against the elastic forces of the first and second compression springs 48 and 50. Accordingly, the operation force is increased in stages when the pressing section 38 comes into contact with the push rod 40.

Thus, the needle holding section 16 is set in the adjusting mode, and the gripping force of the anastomotic needle 15 by the gripping surface 46 of the tube 36 and the gripping member 44 is weakened by the outward pressing force of the sufficiently compressed second compression spring 50 to the push rod 40. In this state, in the body cavity, while the anastomotic needle 15 is gripped by the needle holding section 16, the anastomotic needle 15 is held by using another forceps or the like to adjust its position, direction or the like with respect to the needle holding section 16. After this adjustment, the pressing of the opening/closing lever 20 is released, and the needle holding section 16 is set in the gripping mode again to firmly grip the anastomotic needle 15.

When the anastomotic needle 15 is removed from the needle holder 10, the anastomotic needle 15 is held by another forceps or the like. Then the opening/closing lever 20 is pushed in until it abuts on the stopper 32 to set the needle holding section 16 in a releasing mode and release the gripping of the anastomotic needle 15 by the gripping member 44 and the gripping surface 46, and the anastomotic needle 15 is remove.

Therefore, the needle holder 10 of the embodiment provides the following advantages. According to the needle holder 10 of the embodiment, by adjusting the pushing-in amount of the opening/closing lever 20, the needle holding section 16 can be switched among the gripping mode of gripping the anastomotic needle 15 to enable anastomosing treatment, the adjusting mode of gripping the anastomotic needle 15 by a gripping force lower than that in the gripping mode to enable adjustment of the position, the direction or the like of the anastomotic needle 15 while the anastomotic needle 15 is gripped, and the releasing mode of releasing the anastomotic needle 15. Thus, shifting of the anastomotic needle 15 with respect to the needle holding section 15 is prevented during the anastomosing treatment, the position, the direction or the like of the anastomotic needle 15 with respect to the needle holding section 16 can be adjusted without removing the anastomotic needle from the needle holding section 16, thus operability of the needle holder 10 is improved.

The operation force necessary for pushing in the opening/closing lever 20 is increased in stages when the needle holding section 16 switches from the gripping mode to the adjusting mode. In other words, the state change of the needle holding section 16 is fed back to the operator, thereby improving the operability of the needle holder 10 more.

Furthermore, by the first compression spring 48, the gripping member 44 is pressed in the closing direction to hold the needle holding section 16 in the gripping mode. By the slide bearing 33 and the pressing section 38, the gripping member 44 is moved in the opening direction against the elastic force of the first compression spring 48 to switch the needing holding section 16 among the gripping mode, the adjusting mode, and the releasing mode. When the needle holding section 16 is between the gripping mode and the adjusting mode, the force against the elastic force of the second compression spring 50 mainly becomes an operation force necessary for pushing in the opening/closing lever 20. When the needle holding section 16 is between the adjusting mode and the releasing mode, the force against the elastic forces of the first and second compression springs 48, 50 mainly becomes an operation force necessary for pushing in the opening/closing lever 20. The operation force increases in stages when the needle holding section 16 switches from the gripping mode to the adjusting mode. Hence, according to the embodiment, without increasing complexity, size and weight of the needle holder 10, the switching of the needle holding section 16 among the gripping mode, the adjusting mode, and the releasing mode is realized, and the feeding-back of the state change of the needle holding section 16 to the operator is realized.

When the elastic force of the first compression spring 48 is sufficiently larger than that of the second compression spring 50, the operation force is sufficiently increased during switching from the gripping mode to the adjusting mode. Hence, the operator can surely sense the state change of the needle holding section 16.

According to the embodiment, the elastic force of the first compression spring 48 is set larger than that of the second compression spring 50. However, the elastic force of the first compression spring 48 may be set smaller than that of the second compression spring 50 in accordance with design of the needle holding section 16.

Figure 4:
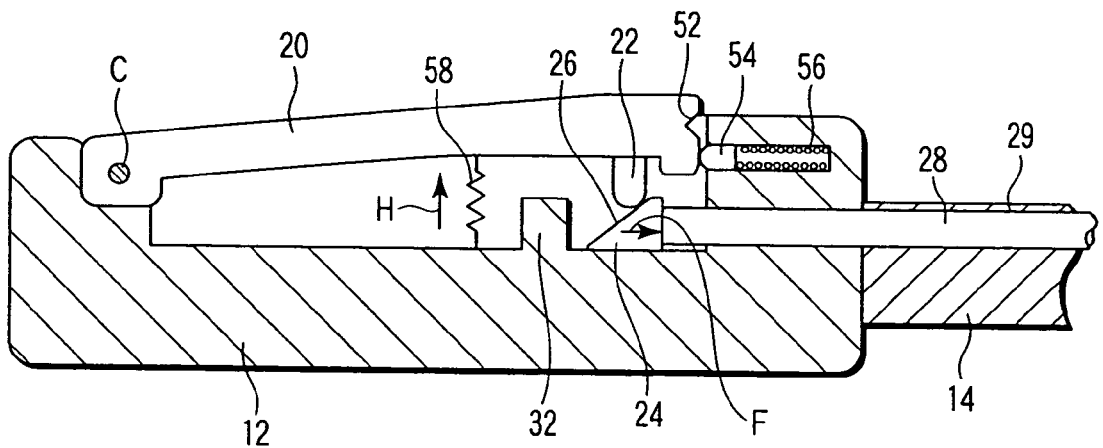
FIG. 4 is a longitudinal sectional view of an opening/closing lever and its surroundings in a needle holder according to a second embodiment of the present invention.
Figure 5:
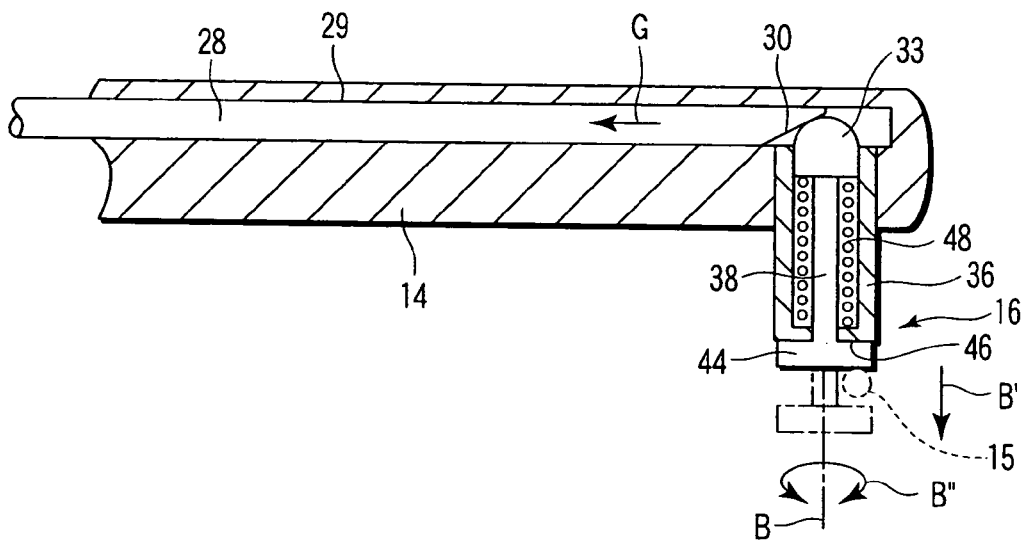
FIG. 5 is a longitudinal sectional view of a distal end part of an insertion section in the needle holder of the second embodiment of the present invention.

FIGS. 4 and 5 show a second embodiment of the present invention. Components having functions similar to those of the first embodiment will be denoted by similar reference numerals, and description thereof will be omitted. A needle holder of the embodiment uses a click mechanism of feeding back switching from a gripping mode to an adjusting mode to an operator by a clicking sense.

As shown in FIG. 4, a click groove 52 is formed in an end surface of a rotation end of an opening/closing lever 20. In a body section 12, a click pin 54 that engages the click groove 52 is arranged to face the click groove 52. This click pin 54 is pressed toward the opening/closing lever 20 by a third compression spring 56 incorporated in the body section 12.

Referring to FIGS. 4 and 5, a fourth compression spring 58 is arranged between the body section 12 side of the opening/closing lever 20 and the body section 12. In a normal mode in which a needle holding section 16 is not operated, the opening/closing lever 20 is pushed up to a maximum limit (direction of an arrow H) by the fourth compression spring 58 to be arranged in a standby position. In this state, the click pin 54 is pressed to the end surface of the rotation end of the opening/closing lever 20 on the body section 12 side rather than in the clock groove 52.

In the needle holding section 16 of the embodiment, neither of the push rod 40 and the second compression spring 50 (see FIG. 3) is used, and a distal end of a pressing section 38 is connected to a gripping member 44. A first compression spring 48 is disposed around the pressing section 38 between an outer end surface of a slide bearing 33 and an inner surface of an outer end wall of a tube 36.

In a gripping mode in which an anastomotic needle 15 is gripped by the needle holding section 16 to enable anastomosis processing, the slide bearing 33 is pressed inward by an elastic force of the first compression spring 48, the gripping member 44 is pressed inward, and the anastomotic needle 15 is firmly gripped by the gripping member 44 and a gripping surface 46. The opening/closing lever 20 is pressed outward by the fourth compression spring 58 to be held in a standby position. As in the case of the normal mode, the click pin 54 is pressed to the end surface of the rotation end of the opening/closing lever 20 on the body section 12 side rather than in the click groove 52.

In an adjusting mode in which the anastomotic needle 15 is gripped by the needle holding section 16 to be adjusted in arrangement, the opening/closing lever 20 is pushed in more than that in the gripping mode so that the click groove 52 can be aligned with the click pin 54. The click pin 54 is pushed into the click groove 52 by an elastic force of the third compression spring 56 to be engaged.

A push pin 22 of the opening/closing lever 20 applies a force to a slope block 24 and a slide rod 28 to push forward the same, and a second slope 30 of the slide rod 28 applies an outward force to the slide bearing 33 to counter the elastic force of the first compression spring 48. Accordingly, while a gripping force of the anastomotic needle 15 by the gripping member 44 and the gripping surface 46 is reduced, almost no change occurs in a gap amount between the gripping member 44 and the gripping surface 46, and thus gripped state of the anastomotic needle 15 is held. Thus, while the gripped state of the anastomotic needle 15 is held, it is possible to adjust a position, a direction or the like of the anastomotic needle 15 with respect to the needle holding section 16.

In a releasing mode in which the anastomotic needle 15 is released from the needle holding section 16, the opening/closing lever 20 abuts on a stopper 32 disposed to project in the body section 12 between the body section 12 side of the opening/closing lever 20 and the body section 12. The click pin 54 is pressed to the end surface of the rotation end of the opening/closing lever 20 on the outside of the click groove 52. As indicated by a dotted line in FIG. 5, the gripping member 44 is opened from the gripping surface 46 so that an opening width can larger than a thickness of the anastomotic needle 15.

Next, an operation of the needle holder 10 of the embodiment will be described. When the anastomotic needle 15 is fixed to the needle holding section 16, the opening/closing lever 20 is pushed in to a maximum limit until it abuts on the stopper 32. In this case, the click pin 54 moves to cross the click groove 52 from the body section 12 side of the click groove 52 to the outside of the same. As a result, a gap is opened to a maximum limit between the gripping member 44 and the gripping surface 46, and the anastomotic needle 15 is arranged in the gap between the gripping member 44 and the gripping surface 46. In this state, when pressing of the opening/closing lever 20 is released, the gripping member 44 is closed by the elastic force of the first compression spring 48, the anastomotic needle 15 is gripped between the gripping member 44 and the gripping surface 46, and the needle holding section 16 is set in the gripping mode.

When a position, a direction or the like of the anastomotic needle 15 with respect to the needle holding section 16 is changed, the opening/closing lever 20 is pushed in and, when clicking such as a click feeling or a clicking sound is sensed, the pushing-in of the opening/closing lever 20 is stopped. In this state, the click pin 54 is engaged with the click groove 52. An outward force is applied from the opening/closing lever 20 to the slide bearing 33 to counter the elastic force of the first compression spring 48, and a gripping force of the anastomotic needle 15 by the gripping member 44 and the gripping surface 46 is reduced. On the other hand, a gap amount between the gripping member 44 and the gripping surface 46 is kept roughly equal to the thickness of the anastomotic needle 15. In a state in which the anastomotic needle 15 is gripped by the gripping member 44 and the gripping surface 46, the position, the direction or the like of the anastomotic needle 15 with respect to the needle holding section 16 is adjusted.

Thus, the needle holder 10 of the embodiment provides the following advantages. According to the needle holder 10 of the embodiment, by the click pin 54 and the click groove 52, a clicking feeling is fed back to the operator when the needle holding section 16 is switched from the gripping mode to the adjusting mode. Hence, a change from the gripping mode to the adjusting mode can be sensed by a clicking sound or the like in addition to the clicking sense, whereby the mode change can be surely sensed.

The needle holder of each of the embodiments can be used not only for the operation under the endoscopic observation but also for an abdominal operation. The present invention is not limited to the needle holders of the embodiments. It can be applied to various surgical grippers which grip instruments. For example, the invention can be applied to a gripping forceps which uses a pair of rotary gripping members having a proximal end pivotally supported thereon to be mutually rotated.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A surgical gripper comprising:
an insertion section including a distal end section and a proximal end section and configured to be inserted into a cavity in a body;
a body section provided on the proximal end section of the insertion section and configured to be held and operated by an operator;
a gripping section provided on the distal end section of the insertion section and configured to grip a treatment member, wherein
a body section includes an operating section movable in an opening and a closing direction between a non-operating position on a closing direction side and a maximum-operating position on an opening direction side and configured to be operated in the opening direction by the operator,
the insertion section includes a transmitting member movable in the opening and the closing direction,
the gripping section includes:
a movable member movable in the opening and the closing direction between a closing position in which the movable member grips the treatment member and an opening position in which the movable member releases the treatment member;
a first elastic member urging the movable member in the closing direction;
an operating member provided between the movable member and the transmitting member, the operating member being movable in the opening and the closing direction and being configured to be switched between a separating state in which the operating member is disposed at the closing direction side and separated from the movable member and a contacting state in which the operating member is disposed at the opening direction side and is in contact with the movable member, the operating member being configured to be urged in the opening direction through the transmitting member when the operating section is operated in the opening direction and configured to urge the movable member in the opening direction when the operating member is in the contacting state and urged in the opening direction; and
a second elastic member provided between the movable member and the operating member, the second elastic member being deformable in the opening and the closing direction and being configured to generate an elastic force smaller than an elastic force of the first elastic member, the second elastic member urging the movable member in the opening direction and urging the operating member in the closing direction to urge the operating section in the closing direction through the transmitting member,
and wherein
the surgical gripper is configured to take following modes:
a gripping mode when the operating section is disposed in the non-operating position, in which the operating section is urged in the closing direction by the second elastic member to be kept in the non-operating position, the movable member is urged in the closing direction by the first elastic member to be kept in the closing position, and the treatment member is gripped in the gripping section by a gripping force such that treatment is performable on tissue by the treatment member gripped in the gripping section;
an adjusting mode when the operating section is disposed between the non-operating position and a switching position, in which the operating member moves from the separating state to the contacting state upon operation of the operating section, and, by operating the operating section in the opening direction against the elastic force of the second elastic member, the second elastic member is deformed to be compressed, the movable member is urged in the opening direction by the second elastic member against the elastic force of the first elastic member, the gripping force with respect to the treatment member in the gripping section is decreased while the movable member is kept in the closing position, and the treatment member is gripped in the gripping section by the gripping force such that an arrangement of the treatment member gripped in the gripping section is adjustable;

a releasing mode where the operating section is disposed between the switching position and the maximum-operating position, in which the operating member is in the contacting state, and, by operating the operating section in the opening direction against the elastic force of the first and the second elastic member, the movable member is moved in the opening direction by the operating member to be disposed in the opening position, and the treatment member is released from the gripping section, and wherein an operating force necessary for operating the operating section is switched from force against the elastic force of the second elastic member to force against the elastic force of the first and the second elastic member in the switching position when the opening section is operated in the operating direction.

* * * * *